United States Patent
Kim et al.

(10) Patent No.: US 10,251,936 B2
(45) Date of Patent: Apr. 9, 2019

(54) EBV ANTIGEN SPECIFIC T-CELL RECEPTOR AND USE THEREOF

(71) Applicant: THE CATHOLIC UNIVERSITY OF KOREA INDUSTRY—ACADEMIC COOPERATION FOUNDATION, Seoul (KR)

(72) Inventors: Tai Gyu Kim, Seoul (KR); Hyun Il Cho, Gyeonggi-do (KR)

(73) Assignee: The Catholic Unviersity of Korea Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 15/974,647

(22) Filed: May 8, 2018

(65) Prior Publication Data
US 2018/0326003 A1    Nov. 15, 2018

Related U.S. Application Data

(62) Division of application No. 14/928,762, filed on Oct. 30, 2015, now Pat. No. 9,993,526.

(30) Foreign Application Priority Data

Sep. 1, 2015   (KR) ........................ 10-2015-0123823

(51) Int. Cl.
*A61K 38/17* (2006.01)
*C07K 14/70* (2006.01)
*C07K 14/725* (2006.01)

(52) U.S. Cl.
CPC ...... *A61K 38/1774* (2013.01); *C07K 14/7051* (2013.01); *C12N 2710/16211* (2013.01); *C12N 2710/16222* (2013.01); *C12N 2740/16043* (2013.01)

(58) Field of Classification Search
None
See application file for complete search history.

(56) References Cited

U.S. PATENT DOCUMENTS

| 6,723,695 | B1 * | 4/2004 | Burrows | C07K 14/005 435/320.1 |
| 8,071,561 | B2 * | 12/2011 | Sallberg | A61K 39/29 424/199.1 |
| 2003/0152582 | A1 | 8/2003 | Burrows et al. | |
| 2013/0116167 | A1 * | 5/2013 | Morgan | C07K 14/7051 514/2.3 |

FOREIGN PATENT DOCUMENTS

KR   10-2012-0074291 A   7/2012

OTHER PUBLICATIONS

Korean Patent Application No. 10-2015-0123823, Office Action dated May 12, 2017, 5 pages.
U.S. Appl. No. 14/928,762, Office Action dated Sep. 20, 2017, 12 pages.

* cited by examiner

*Primary Examiner* — Agnieszka Boesen
(74) *Attorney, Agent, or Firm* — Leydig, Voit & Mayer, Ltd.

(57) ABSTRACT

The present invention relates to an EBV antigen specific T-cell receptor and the use thereof. Specifically, the present invention provides T cells specific for LMP1 of EBV using a T-cell receptor which is highly specific for specific epitopes derived from an EBV antigen, LMP1. In addition, the EBV antigen specific T-cell can be used in the prevention or treatment of EBV-associated diseases.

5 Claims, 7 Drawing Sheets
Specification includes a Sequence Listing.

EBV ANTIGEN SPECIFIC T-CELL RECEPTOR AND USE THEREOF

CROSS-REFERENCE TO RELATED APPLICATION

This application is a divisional application of U.S. application Ser. No. 14/928,762, filed Oct. 30, 2015, which claims priority to Korean Patent Application No. 10-2015-0123823, filed Sep. 1, 2015, the disclosures of which are incorporated herein by reference in their entireties.

BACKGROUND

1. Field of the Invention

The present invention relates to an EBV antigen specific T-cell receptor which is capable of producing TCR-modified T cells specific for epitopes derived from a latent membrane protein 1 (LMP1) of an Epstein-Barr virus (EBV) and the use thereof.

2. Discussion of Related Art

The number of patients clinically diagnosed as suffering from tumors has recently been increasing due to environmental changes, aging of the population, improvement in diagnostic technology, etc. However, it is difficult to perfectly remove tumors by just using the conventional palliative therapies for tumors because a micrometastatic tumor cell acquires a tolerance due to its genetic instability. Accordingly, there arises a need to develop new immunotherapies that help to overcome the limitations of conventional tumor therapies and an effective general-purpose method for the treatment of tumors using the same.

EBV belongs to the herpesvirus family, and 90% or more of normal people become infected with EBV. EBV is usually established by a latent infection without symptoms, but in patients whose immune system is impaired over a long period of time due to a bone marrow or organ transplant, EBV is known to cause cancer such as lymphoproliferative diseases, Burkitt's lymphoma, nasopharyngeal carcinoma (NPC), Hodgkin's disease, etc. Lymphocyte disorders associated with EBV infection include post-transplant lymphoproliferative diseases (PTLDs) that occur after transplantation in extranodal NK/T-cell lymphoma, nasal type, including Hodgkin's lymphoma. The lymphoproliferative disease, which is a non-Hodgkin's lymphoma type, is present with various manifestations ranging from benign diseases, such as polyclonal B-cell lymphocytosis, to malignant diseases, such as malignant lymphoma, as the proliferation of lymphocytes or plasma cells occurs as a result of EBV latency in the donor and the continued administration of immune inhibitors following solid organ or hematopoietic stem cell transplantation. The lymphoproliferative disease is a severe complication occurring throughout the whole body in 1-15% of organ transplant patients. It was recently confirmed that EBV genes are expressed in some patients with gastric cancer—in Japan and Korea, 5-10% of patients with gastric cancer. A research team at the University of Kagoshima analyzed the distribution of EBV-positive gastric cancer in seven countries, including Japan, and found that the odds ratios of EBV-associated gastric cancer were higher in Russia (1.9), Colombia (2.5), Chile (2.7), etc., compared to that in Japan (1.0).

Conventional treatments of EBV-associated tumors include reduction of immune inhibitor administration, use of antiviral agents, anticancer chemotherapy, and administration of rituximab. However, responses to such conventional treatments vary and an effective treatment for EBV-associated tumors has not been found yet. Thus, it is urgent to develop a new treatment for EBV-associated tumors.

For adoptive immunotherapy using EBV antigen-specific T cells, Dr. Brenner's group conducted a study to find a method for treating EBV infections or EBV-associated tumors, such as EBV-associated lymphoma or throat cancer, by inducing CTLs specific for EBV antigens in vitro and transplanting hematopoietic stem cells. In Korea, the research group including the present inventors has succeeded initially in treating patients with EBV-positive lymphoma and acute leukemia using adoptive immunotherapy with antigen-specific T cells. The adoptive immunotherapy using antigen-specific T cells cultured in vitro would help to overcome the limitations of an antibody drug. However, despite such an advantage of the adoptive immunotherapy, the costs for culturing antigen-specific T cells with high avidity in vitro which recognize and remove tumor cells by overcoming immune tolerance to an tumor-associated antigen are highly expensive, which is hindering its clinical applications for general purposes and commercialization.

Recently, there has been a lot of research on targeted immunotherapy using gene-engineered T cells as adoptive immunotherapy to overcome the limitations of antibody drugs, cellular tumor vaccine, and adoptive cellular immunotherapy for treating tumor patients. In particular, it is expected that general-purpose targeted immunotherapy at the off-the-shelf stage which overcomes the limitations of tailor-made therapies can be developed by using TCRs specific for tumor antigens. However, due to difficulties in obtaining antigen-specific clones of T cells in order to obtain antigen-specific TCR genes and cloning the TCR genes, the development has only been modest in Korea and relevant clinical trials have been conducted by foreign researchers on a limited basis.

SUMMARY OF THE INVENTION

The present invention is directed to provide a T-cell receptor (TCR) which is highly specific for epitopes derived from an EBV antigen, LMP1.

Also, the present invention is directed to provide nucleotide sequences encoding the TCR, a vector including the nucleotide sequences, and the use thereof to produce EBV-specific T cells.

Also, the present invention is directed to provide the use of EBV-specific T cells in adoptive immunotherapy.

In one aspect, the present invention provides a T-cell receptor capable of binding to a peptide derived from a latent membrane protein 1 (LMP1) of an Epstein-Barr Virus (EBV) on being presented by a major histocompatibility complex (MHC), wherein the peptide is represented by an amino acid sequence set forth in SEQ ID NO: 1.

The present invention also provides nucleotide sequences encoding the TCR.

The present invention also provides a vector including the nucleotide sequences.

The present invention also provides a host cell transformed with the vector.

The present invention also provides a composition for prevention or treatment of EBV-associated diseases, including the vector or the host cell.

The present invention also provides the use of the vector or the host cell in the production of drugs used to prevent or treat EBV-associated diseases.

The present invention also provides a method for treating EBV-associated diseases in a subject in need thereof, comprising administering a composition for preventing or treating EBV-associated diseases including a pharmaceutically effective amount of the vector or the host cell to the subject in need thereof.

The present invention can provide a T cell specific for EBV LMP1 antigen by using a T cell receptor highly specific for epitopes derived from LMP1 of EBV.

The T cells specific for EBV LMP1 antigens can be applied to adoptive immunotherapy in order to prevent or treat EBV-associated diseases, such as EBV-positive Hodgkin lymphoma, EBV-positive nasopharyngeal carcinoma, EBV-positive post-transplant lymphoproliferative diseases (PTLDs).

DETAILED DESCRIPTION OF EXEMPLARY EMBODIMENTS

Figure 1:
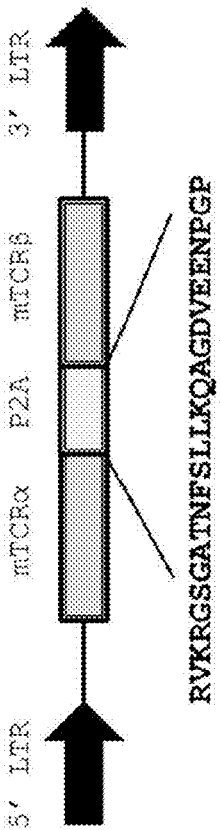
FIG. 1 shows the structure of a lentiviral vector including the EBV LMP-1*166 S4-12 gene of the present invention and the amino acid sequence of LMP1*166 S4-12 TCRAlpha P2A TCRBeta.

The present inventors completed this invention through the processes of securing mouse-derived TCR genes (S4-12) which are highly specific for $LMP1_{166-174}$ epitopes derived from an EBV antigen, LMP1, transferring them to human T cells by using recombinant viruses, confirming the antigenic specificity of the T cells, and confirming the anti-tumor ability of the T cells by using immunodeficient mice.

Therefore, the present invention provides a T-cell receptor capable of binding to a peptide derived from a latent membrane protein 1 (LMP1) of an Epstein-Barr Virus (EBV) on being presented by a major histocompatibility complex (MHC), wherein the peptide is represented by an amino acid sequence set forth in SEQ ID NO: 1.

As used herein, the terms "T-cell receptor" and "TCR" refer to a molecule found on the surface of the T cell responsible for recognizing the antigens that bind to MHC molecules, and customarily refer to a molecule capable of recognizing a peptide when presented by a MHC molecule. The molecule is a heterodimer including α and β chains (or selectively, γ and δ chains) or a TCR construct that generates signals. The TCR of the present invention is a hybrid TCR including the sequences derived from other species. For example, as mouse TCRs are more effectively expressed than human TCRs in human T cells, the TCR includes a human variable region and a murine constant region.

The TCR includes two chains (α and β chains), each including three complementarity determining regions (CDRs).

The three CDRs in α and β chains are as follows:

CDR1α - (DPNSYY) SEQ ID NO: 3

CDR2α - (VFSSTEI) SEQ ID NO: 4

CDR3α - (AVSGTGGYKVV) SEQ ID NO: 5

CDR1β - (KGHPV) SEQ ID NO: 7

CDR2β - (FQNQEV) SEQ ID NO: 8

CDR3β - (ASNQLGSSYEQY) SEQ ID NO: 9

The above CDRs may include one or more "modifications" in the given amino acid sequences, such as substitution, addition, or deletion.

In addition, the α-chain of TCR as described in the present invention may have the amino acid sequence set forth in SEQ ID NO: 2 or variation sequences with amino acid sequence homologies of at least 70%, 80%, 90%, or 95%. The β-chain of TCR as described in the present invention may have the amino acid sequence set forth in SEQ ID NO: 6 or variation sequences with amino acid sequence homologies of at least 70%, 80%, 90%, or 95%. The variation sequence includes an addition, deletion, and/or insertion of amino acids. The variations may be made mainly around one or more regions, for example around a constant region, a linker, or a framework region of the α-chain or β-chain, and also may be located on the region of the whole molecule. Comparison of homology can be conducted by using a program for visible comparison of sequences, which is readily available. This commercially available computer program can assess the percentage of homology between two or more sequences. Examples of such programs that can conduct a comparison of homology include, but are not limited to, BLAST package (Ausubel et al., 1999 ibid—see Chapter 18), FASTA (Atschul et al., 1990, J. Mol. Biol., 403-410), and GENEWORKS suite of comparison tools. In addition, a sequence may contain a deletion, insertion, or substitution of amino acid residues, resulting in a silent change, thereby generating functionally equivalent variants. Intentional amino acid substitutions can occur based on the polarity, electric charge, solubility, hydrophobicity, hydrophilicity, and/or amphipathic properties of the residues, provided that secondary substrate binding activity is maintained. For example, negatively charged amino acids include aspartic acid and glutamic acid; positively charged amino acids include lysine and arginine; and amino acids having an uncharged polar head group with a similar level of hydrophilicity include leucine, isoleucine, valine, glycine, alanine, asparagine, glutamine, serine, threonine, phenylalanine, and tyrosine. Further, substitution used herein may refer to a substitution occurring in two homologous sequences, such as basic for basic, acidic for acidic, polar for polar, etc. Non-homologous substitutions occur from one class of residue to another or alternatively involving the inclusion of unnatural amino acids such as ornithine, diaminobutyric acid, norleucine, ornithine, pyriylalanine, thienylalanine, naphthylalanine, and phenylglycine.

The TCR of the present invention recognizes a full or partial amino acid sequence of LMP-$1_{166\text{-}174}$ of EBV (TLL-VDLLWL: SEQ ID NO: 1). The TCR can recognize partial sequences of one or more (up to five) amino acids in an upstream or downstream region.

The TCR, a peptide-MHC complex, binds to a peptide. An MHC molecule is an MHC class I or II molecule. A complex is located on the surface of an antigen presenting cell, such as a dendritic cell or B cell, and can be fixed by, for example, being coated with a bead or plate. The human leukocyte antigen system is the name of the human major histocompatibility complex (MHC), and includes HLA class I antigens (A, B & C) and HLA class II antigens (DP, DQ, & DR).

The present invention relates to a nucleotide sequence encoding the TCR.

The nucleotide sequence is single- or double-stranded, and is an RNA or DNA sequence. The nucleotide sequence may be a codon-optimized sequence. Codon usage varies among different cells. The codon usage bias corresponds to the relative frequency bias of specific tRNAs in a cell. The codons of sequences can be adjusted such that the relative frequencies of codons correspond to those of tRNA, and this could allow an increase in the expression.

Many types of viruses including HIV and lentiviruses use many rare codons, and modify those corresponding to the commonly used codons of mammals, thereby increasing the expression of packaging components in mammalian production cell lines. Codon usages in many different organisms including mammals are well known in the art. Moreover, codon optimization is related to the reduction of unstable mRNA motifs and complicated splice sites.

The nucleotide sequence of the present invention may contain the nucleotide sequence encoding the α-chain of TCR represented by a base sequence set forth in SEQ ID NO: 10, the nucleotide sequence encoding the β-chain of TCR represented by a base sequence set forth in SEQ ID NO: 14, or variation sequences encoding the variant with amino acid sequence homologies of at least 70%, 80%, 90%, or 95%.

In addition, the nucleotide sequence of the present invention may contain the nucleotide sequence encoding the three CDRs in α and β chains:
CDR1α: SEQ ID NO: 11
CDR2α: SEQ ID NO: 12
CDR3α: SEQ ID NO: 13
CDR1β: SEQ ID NO: 15
CDR2β: SEQ ID NO: 16
CDR3β: SEQ ID NO: 17

The above variation sequences include an addition, deletion, or substitution of one or more bases. The variants, which contain an addition or deletion, balance themselves (i.e., an addition for each deletion) such that the variation does not cause a frameshift in the variation of remaining sequences. The entire or partial variation is "silent" in "send" which does not affect the sequence of an encoded protein due to degeneracy of the protein code. As described above, the entire or partial variation causes amino acid substitutions. The variation may be made mainly around one or more regions, for example around a constant region, a linker, or a region encoding the framework of α-chain or β-chain, and also may be located inside a molecule.

The variation sequences should be capable of encoding the full or partial sequence that combines TLLVDLLWL (SEQ ID NO: 1):MHC complex.

The present invention also relates to a vector including nucleotide sequences.

As used herein, the term "vector" refers to a nucleic acid molecule that is capable of transmitting another nucleic acid attached to it. "Plasmid," a type of vector, refers to a circular, double-stranded DNA loop which is capable of ligating an additional DNA fragment. A viral vector, another type of vector, is capable of ligating an additional DNA fragment with a viral genome. Some vectors (e.g., bacterial vectors having the origin of bacterial replication and episomal mammalian vectors) can self-replicate in host cells when introduced thereinto. When introduced into host cells, other types of vectors (e.g., nonepisomal mammalian vectors) can become incorporated into and replicated with the host genome. In addition, some other vectors can direct the expression of operably linked genes. Such a vector is referred to herein as "recombinant expression vector" (or simply as "expression vector"). The expression vectors which are generally employed in the recombinant DNA technique are plasmid vectors. As the plasmid vector is the most common type of vector, "plasmid" and "vector" are often used interchangeably. However, the vectors of the present invention include other type of vectors such as viral vectors with the same functions (e.g., adenoviral vectors, adeno-associated viral vectors (AAVV), herpesvirus vectors, retroviral vectors, lentivirus vectors, baculovirus vectors).

The retrovirus is an RNA virus whose life cycle is different from that of a lytic virus. In this respect, the retrovirus can be regarded as a contagious entity that replicates through a DNA intermediate. When the retrovirus infects a cell, the genome is converted into DNA by a reverse transcriptase enzyme. A DNA copy is used as a template for the production of proteins encoded by the viruses necessary for the assembly of new RNA genomes and infectious viral particles. Examples of retroviruses include murine leukemia virus (MLV), human immunodeficiency virus (HIV), equine infectious anemia virus (EIAV), mouse mammary tumor virus (MMTV), Rous sarcoma virus (RSV), Fujinami sarcoma virus (FuSV), Moloney leukemia virus (Mo-MLV), FBJ murine osteosarcoma virus (FBR MSV), Moloney murine sarcoma virus (Mo-MSV), Abelson murine leukemia virus (A-MLV), avian myelocytomatosis virus 29 (MC29), avian erythroblastosis virus (AEV), and all other retroviruses including lentiviruses. Coffin et al. ("Retroviruses" 1997 Cold Spring Harbour Laboratory Press Eds: J M Coffin, SM Hughes, HE Varmus, pp. 758-763) provides a detailed list of retroviruses.

Further, lentiviruses belong to a class of retroviruses, but they are capable of infecting both differentiated and undifferentiated cells (Lewis et al. (1992) EMBO J. 3053-3058).

A viral particle is surrounded with an amphotropic envelope or a gibbon ape leukemia virus envelope so as to effectively infect human cells. An increase in the supply of CD3 molecules leads to an increase in the expression of TCRs in gene-modified cells. Thus, a vector may include genes for CD3-gamma, CD3-delta, CD3-epsilon, and/or CD3-zeta. The vector includes only genes for CD3-zeta. Genes are connected by self-cleaving sequences such as 2A self-cleaving sequences. In addition, one or more separated vectors are provided in order to encode CD3 genes for a common transfer having a TCR-encoding vector.

The present invention also relates to a host cell transformed with the vector.

The host cell expresses the TCR of the present invention. The host cell may be a T cell. Preferably, the host cell is derived from a T cell separated from a subject. The T cell is a part of the mixed cell population separated from a subject, such as peripheral blood lymphocytes (PBLs). T cells in PBLs can be activated by using any of well known methods in the art, for example, by using anti-CD3 and anti CD28 antibodies.

The T cell is a CD4+T helper cell or CD8+ cytotoxic T cell. Cells are present in a mixed group of CD4+T helper cells and CD8+ cytotoxic T cells. For example, the multiclonal activation using anti-CD3 antibodies selectively combined with anti-CD28 antibodies induces the proliferation of CD4+ and CD8+ T cells, but also induces the proliferation of CD4+25+ regulatory T cells. It is undesirable that the transfer of TCR genes into regulatory T cells inhibits the activation of gene-modified cytotoxic and T helper cells. Thus, CD4+CD25+ populations drastically decrease before the transfer of TCR genes.

The present invention also relates to a composition for the prevention or treatment of EBV-associated diseases, including the vector or the host cell.

Moreover, the present invention provides the use of vector or host cell in the production of the drugs for the prevention or treatment of EBV-associated diseases.

EBV-specific T cells recognize LMP-1 proteins. EBV-specific T cells recognize an epitope TLLVDLLWL (SEQ ID NO: 1).

As used herein, the term "prevention" refers to averting, delaying, impeding, or hindering disease. Treatment refers, for example, to preventing or reducing the possibility of EBV infection.

As used herein, the term "treatment" refers to caring for a subject with a disease to ameliorate, treat, or reduce symptoms or to delay or stop the progress of the disease, and also refers to the therapy that helps a subject infected with the virus go into a noninfectious condition. The treatment reduces the EBV viral load.

EBV-specific T cells can be used for treating any type of EBV-associated disease, and express LMP-1 antigens. For example, EBV-specific T cells can be used for treating EBV-positive Hodgkin's lymphoma, EBV-positive nasopharyngeal cancer, or EBV-positive post-transplant lymphoproliferative diseases (PTLDs). PTLD occurs following allogeneic HSCT after solid organ (kidney, heart, lung, and liver) transplantation. Burkitt's lymphoma is a pediatric cancer most often seen in equatorial Africa. Characteristically, the jaw is most often affected. A genetic study confirmed that Burkitt's lymphomas found in equatorial Africa—over 95% of children in equatorial Africa are infected with EBV at around age 3—were mainly derived from EBV infectious lymphomas. A Hodgkin's lymphoma characteristic is that it spreads from a lymph node methodically to other lymph nodes and that it spreads out to the whole body in its advanced stage. EBV genes were found in up to 50% of patients with Hodgkin's lymphoma in specific regions. Nasopharyngeal cancer is one of the most common cancers in South China. The areas principally affected are the nasopharynx, pharynx, and the top of the throat, and nasal passages and auditory tubes connecting the remaining parts of the upper respiratory tract. Post-transplant lymphoproliferative disease (PTLD) relates to a variety of conditions that may occur in humans following organ transplantation. EBV viruses are associated with most PTLD cases. Patients with PTLD exhibit various symptoms ranging from blood cell cancer, such as B-cell lymphoma to increase the number of lymphocytes in the bloodstream. PTLD is an uncontrolled proliferation of B cell lymphocytes after infection with the Epstein-Barr virus. T cell depletion caused by the use of anti-T cell antibodies for the prevention or treatment of graft rejection may increase the risk of PTLD. Multiclonal PTLD may form tumor masses and exhibit symptoms due to a mass effect, e.g., a symptom of bowel obstruction. Monoclonal forms of PTLD tend to form a disseminated malignant lymphoma. The treatment of PTLD is performed voluntarily by reducing or suspending the use of immunosuppressive medications, and antiviral therapy can additionally be applied.

The composition for the prevention or treatment of EBV-associated diseases as claimed in the present invention may further include a pharmaceutically acceptable carrier.

Examples of the pharmaceutically acceptable carrier include, but are not limited to, a carrier and a vehicle both commonly used in the field of medicine, specifically, ion exchange resins, alumina, aluminum stearate, lecithin, serum proteins (e.g., human serum albumin), buffer substances (e.g., various phosphates, glycine, sorbic acids, potassium sorbate, and partial glyceride mixtures of saturated vegetable fatty acids), water, salts or electrolytes (e.g., protamine sulfate, sodium phosphate dibasic, potassium hydrogen kamryum, sodium chloride, and zinc salts), colloidal silica, magnesium trisilicate, polyvinyl polyvinyl pyrrolidone, cellulose-based substrates, polyethylene glycol, sodium carboxymethylcellulose, polyarylates, waxes, polyethylene glycol, and wool fabric and the like.

In addition, the composition of the present invention may further include a lubricant, a wetting agent, an emulsifier, a suspending agent, or a preservative in addition to the above components.

In one aspect, the composition of the present invention can be prepared in an aqueous solution for parenteral administration. Preferably, Hank's solution, a Ringer's solution, or a buffer solution such as a physically buffered saline may be used. A substrate, such as sodium carboxymethyl cellulose, sorbitol, or dextran, which can increase the viscosity of the suspension, may be added to an aqueous suspension for injection.

The composition of the present invention can be administered either systemically or locally, and can be formulated to be suitable for such administration, using well known technologies in the art. For example, the composition can be mixed with an inert diluent or an edible carrier for oral administration, or it may be administered in a pressure type sealed in hard or soft gelatin capsules, or tablets. For oral administration, the active compound is mixed with excipients and can be used in the form of an intake type tablet, a buccal tablet, a troche, a capsule, elixirs, suspensions, syrup, or a wafer.

Various types of injectable, parenteral formulations can be prepared according to known techniques or techniques that are commonly used in the art. The formulation can be administered by intravenous injection, subcutaneous injection, intramuscular injection, intraperitoneal injection, transdermal delivery, etc.

The appropriate dosage of the composition of the present invention is determined by factors such as the mode of administration, age, body weight, sex, disease severity, food, administration time, administration route, elimination rate, and response sensitivity. For example, the daily dosage of the composition of the present invention is 0.1-1000 mg/kg, preferably, 10-100 mg/kg. The composition can be administered once or several times a day.

The present invention also provides a method for treating EBV-associated diseases in a subject in need thereof, comprising administering a composition for preventing or treating EBV-associated diseases including a pharmaceutically effective amount of the vector or the host cell to the subject in need thereof.

A host cell transformed with a vector including the TCR of the present invention or the vector (e.g., T cell) can be used in the treatment of EBV-associated diseases by means of adoptive transfer.

To achieve this, T cells are isolated from a subject for use in the adoptive transfer of genetically modified cells. The genetically modified cells can be prepared by selectively enabling immunotherapy for the subject with T cells isolated from the subject, TCR gene transfer, and adoptive transfer of TCR-transduced cells. T cells isolated from the subject are isolated from another subject akin to that. Cells are isolated from a donor. For example, if a subject is in the middle of receiving or received a solid organ transplant, the cells are derived from a donor.

As the pharmaceutical composition used in the treatment of EBV-associated diseases and the method of administration thereof are already described above, information common between the two is omitted in order to avoid the undue complexity of the specification of the subject application.

Meanwhile, the composition for preventing or treating EBV-associated diseases can be administered to all types of animals, for example, any animal, such as dogs, cats, mice, etc., excluding humans.

Hereinafter, the present invention will be described in further detail with reference to examples. However, these examples are not intended to limit the scope of the present invention.

<Example 1> Preparation of Viral Vector for EBV-Specific TCR Gene (LMP1*166 S4-12) Transfer (Cell Line and Peptide)

An HLA-A2-positive T2 cell line, K562 cell line, 293T cell line, and Jurkat cell line were obtained from ATCC (American Type Culture Collection, USA). All the cell lines were cultured in an RPMI-1640 (GibcoBRL, USA) medium containing 10% FBS (fetal bovine serum), 2 mM L-glutamine, 100 U/ml penicillin, and 100 µg/ml streptomycin (GibcoBRL). To produce recombinant lentiviruses, a 293T cell line was also obtained from ATCC and then cultured in a DMEM (GibcoBRL) medium containing 20% FBS. EBV (Epstein-Barr virus)-transformed B LCLs (lymphoblastoid cell lines) were prepared by EBV transformation in donor PBMCs of HLA-A2 and HLA-A24 subtypes, and then cultured in an RPMI-1640 (GibcoBRL) medium containing 10% FBS. HLA-A*0201 and LMP1 genes were expressed in a K562 cell line using an electric shock kit (Lonza), thereby preparing a cell line (K562/HLA-A2/LMP1) for use in target cells and experimental mouse models.

An HLA-A*0201 subtype-specific peptide used in the experiment, which has a purity of over 90%, was purchased from A&A labs; WT1*126(RMFPNAPYL, SEQ ID NO: 20), LMP1*32(LLLALLFWL, SEQ ID NO: 21), LMP1*92 (LLLIALWNL, SEQ ID NO: 22), LMP1*125(YLLEML-WRL, SEQ ID NO: 23), LMP1*125(YLQQNWWTL, SEQ ID NO: 24), LMP1*166(TLLVDLLWL, SEQ ID NO: 1), LMP1*167(LLVDLLWLL, SEQ ID NO: 25), LMP1*173 (WLLLFLAIL, SEQ ID NO: 26).

(LMP1*166-Specific CD8 T Cell Immune Response in HLA-A*0201 Transgenic Mice)

Transgenic mice [C57Bl/6-Tg(HLA-A2.1)1Enge/J] expressing human HLA-A*0201 genes were purchased from Jackson Laboratory for use in experiments approved by the Animal Experiment Committee of the Catholic University.

In order to induce an LMP1*166-specific CD8 T cell immune response in HLA-A*0201 transgenic mice, myelocytes were collected from femoral bones of transgenic mice at 8-12 weeks of age, and then cultured in a medium containing 20 ng/ml GM-CSF and 10 ng/ml IL-4. Three days later, progenitor cells were removed from suspended non-dendritic cells, and then additionally cultured for 4 days under the same conditions, thereby obtaining dendritic cells. The dendritic cells cultured for 7 days were sensitized by treatment with 10 ng/ml concentration of an EBV-antigen LMP-1 derived HLA-A2 epitope, LMP1*166(TLL-VDLLWL, SEQ ID NO: 1) peptide for 18 hours. $2 \times 10^6$ LMP1*166 peptide sensitized-dendritic cells were injected intravenously into HLA-A*0201 transgenic mice. Seven days later, a vaccine consisting of [150 µg LMP1*166 peptide/50 µg poly-IC/100 µg anti-CD40 antibody] was intravenously injected. Eight days later, CD8 T cells were isolated from mouse spleen cells and then LMP1*166-specific CD8 T monoclonal cells were cultured.

(Cultivation of LMP1*166-Specific CD8 T Monoclonal Cells)

CD8 T cells were isolated from the spleen cells of HLA-A*0201 transgenic mice in which an LMP1*166-specific CD8 T cell immune response were induced, according to magnetic cell sorting (Miltenyi Biotec). The isolated CD8 T cells were sensitized with 5 µg/ml concentration of $1 \times 10^6$ CD8 T cells and then mixed with dendritic cells irradiated at 6,000 rad after being cultured in a culture fluid containing 100 U/ml IL-2 using a 24-well cell culture plate for 7 days. The cells obtained 7 days later were sensitized with 0.5 CD8 T cells per well at a concentration of 1 µg/ml and $2.5 \times 10^4$ per well using a U-bottomed 96-well cell culture plate, and then cultured in a culture plate containing a T2 cell line irradiated at 10,000 rad and mouse spleen-derived cells irradiated with $1 \times 10^5$ X-rays at 7,500 rad using a culture fluid containing 50 µg/ml IL-2 and 5 ng/ml IL-7. The culture fluid was replaced with a new one every day for 7-14 days. The cells proliferated in the culture plate proliferated in a culture plate containing a T2 cell line sensitized at a concentration of 1 µg/ml and irradiated at 10,000 rad in a 48-well cell culture plate and mouse spleen-derived cells irradiated with $1 \times 10^6$ X-rays at 7,500 rad. Then, the LMP1*166-specific T cell response was confirmed by using an IFN-γ secretion assay with peptides, and then RNAs were isolated for TCR cloning.

(LMP1*166-Specific TCR Cloning and Preparation of Recombinant Lentiviruses)

RNA was obtained from $1 \times 10^3$ to $1 \times 10^5$ T cell clones using an RNeasy mini kit of Qiagen, and cDNA was synthesized using a SMART RACE cDNA amplification kit (manufactured by Clontech). PCR products were obtained from cDNA according to the experimental method of the manufacturer using an Advantage 2 PCR kit (manufactured by Clontech), using a TCR-alpha constant region primer, 5'-actggtacacagcaggttctgg-3' (SEQ ID NO: 27), TCR-beta constant region primer, 5'-aaggagaccttgggtggagtc-3' (SEQ ID NO: 28), and then TCR DNA gene sequences at the 5'-termini of TCR-alpha and TCR-beta were analyzed. The sequences are compared using the International Immunogenetics Information System, (www<dot>imgt<dot>org/IMGT_vquest/vquest?livret=0&Option=mouseTcR), and TCR alpha/TCR-beta chain subtypes were confirmed. By using a primer including DNA sequences at the 5'-termini of TCR-alpha/TCR-beta genes, TCR-alpha/TCR-beta chain genes were amplified from cDNA by a PCR method, thereby obtaining DNA sequences.

If TCR alpha and TCR beta are transferred in the state of being apart to express the two genes forming heterodimers in a target cell, the expression rate will vary depending on the transfer rate. Thus, it is important for the two genes to be simultaneously transferred to a single cell so as to be expressed as proteins. The present inventors amplified a single-stranded gene where TCR alpha/beta chains are connected by a PCR method using a 2A amino acid sequence (RVKRGSGATNFSLLKQAGDVEENPGP, SEQ ID NO: 29), which can be divided into two proteins by a proteolytic enzyme after being expressed as amino acids. For this, single-stranded LMP1*166 TCR having the structure of TCR alpha-P2A-TCR beta connected by a P2A amino acid sequence (RVKRGSGATNFSLLKQAGDVEENPGP, SEQ ID NO: 29) was amplified by 2 step PCR using a TCR-alpha reverse primer; 5'-cttccacgtcgccggcctgcttcagcagggagaagttg-gtggcgccgctgcctctcttcactctactggaccacagcctcag cgt-3' (SEQ ID NO: 30); a TCR-beta reverse primer; 5-ttctccctgct-gaagcaggccggcgacgt ggaagaaaaccctggcccc-3' (SEQ ID NO: 31), and a gene with a size of about 1.9 kb and with the structure of LMP1*166 TCR alpha-2A-TCR beta was obtained. DNA sequences were analyzed by cloning the gene into a pCDH lentiviral vector (FIG. 1).

<Example 2> Preparation of EBV LMP-1-specific TCR (LMP1*166 S4-12)-Introduced Human T Cells.

The recombinant lentiviral vectors having the structure of LMP1*166 TCR alpha-2A-TCR beta were used to infect/transfect activated human T cells by obtaining a culture supernatant containing lentivirus particles expressing LMP1*166 TCR genes by lysosome transfer.

To produce the recombinant lentiviruses with the structure of LMP1*166 TCR alpha-2A-TCR beta, $1 \times 10^7$ 293 T cell lines were cultured in a 100 mm culture plate coated with 5 μg/ml of Poly-L of Sigma. 20 hours later, a pCDH-LMP1*166 TCR vector and lentivirus packaging plasmids (psPAX2/pMD2G) were simultaneously transferred to a 293T cell line according to the experimental method of the manufacturer using lipofectamin (manufactured by Invitrogen). 48 hours later, the supernatant was centrifuged and then filtered through a 0.4 μm filter, thereby obtaining/producing recombinant lentiviruses.

Then, to confirm the transfer and expression of LMP1*166 TCR-recombinant lentiviruses to/in human lymphocytes and a Jurkat cell line, lymphocytes were isolated from peripheral blood of a donor and then $5 \times 10^6$ lymphocytes per well were cultured in a culture fluid containing 30 ng/ml anti-CD3(OKT3) antibodies and 300 U/ml IL-2 using a 24-well cell culture plate for 48 hours. 48 hours later, the human lymphocytes and Jurkat cell line, a human T cell lymphoma cell line, were obtained. LMP1*166 TCR-recombinant lentiviruses were added to $1 \times 10^6$ cells per well using a 24-well cell culture plate at an MOI of 0.5-1, and then 5 μg/ml polybrene (manufactured by Sigma) was added and centrifuged at 32° C., 2500 rpm for 60 minutes. Then, a culture fluid containing 300 U/ml IL-2 was added. Two or three days later, the expression of LMP1*166 TCR genes introduced by fluorescence staining using human CD3/CD4/CD8 and mouse TCR beta-specific antibodies was confirmed.

LMP1*166 S4-1, LMP1*166 S4-6, LMP1*166 S4-12 genes cloned from the three types of mouse T cell clones specific for LMP1*166 peptides were transferred to a human T cell lymphoma cell line, the Jurkat cell line, and lymphocytes isolated from human peripheral blood, using lentiviruses, and the levels of LMP1*166 TCR expression were checked.

Figure 2A:
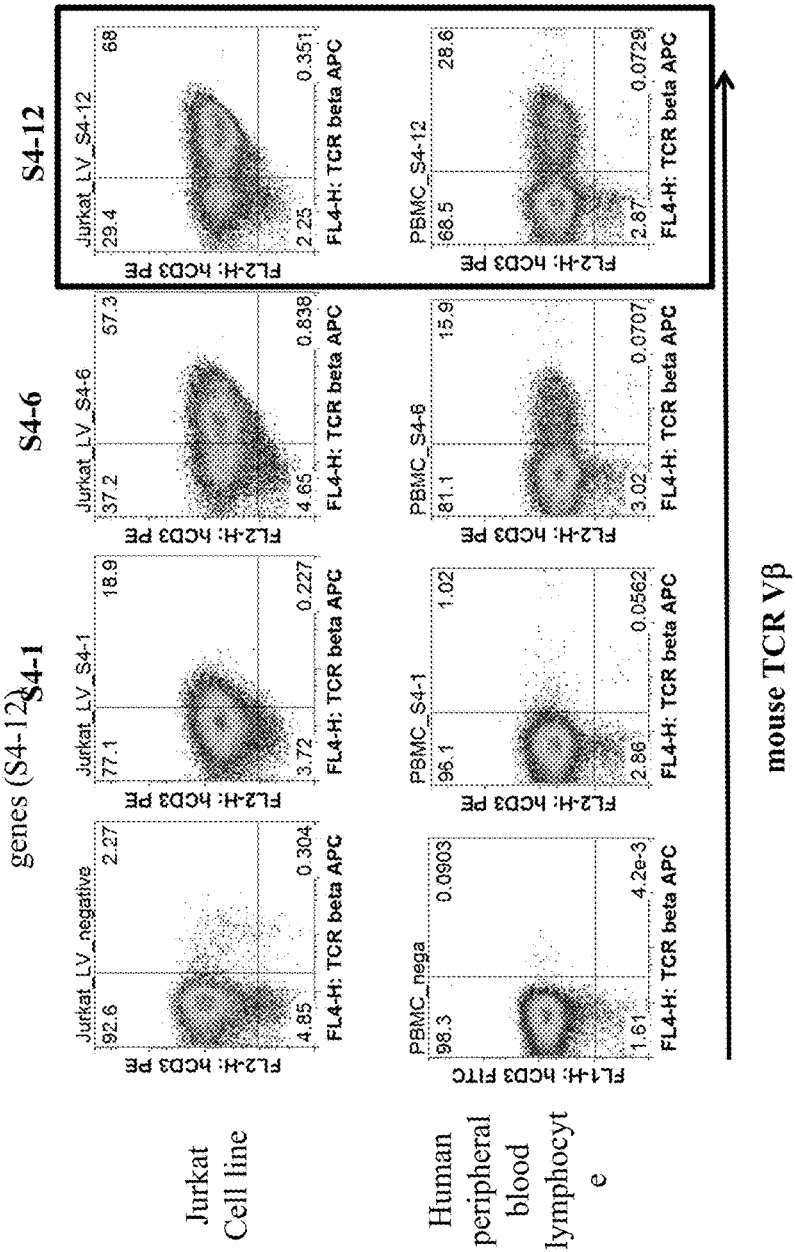
FIGS. 2A-2B shows the rate of expression of TCR (FIG. 2A) in human T cells into which EBV LMP-1-specific TCR (LMP1*166 S4-12) of the present invention is introduced and IL-2 secretion (FIG. 2B) confirming TCR reactions.

As shown in FIG. 2A, the expression levels differed between the Jurkat cell line and human lymphocytes according to a TCR clone, and LMP1*166 S4-12 TCR genes were most highly expressed.

Figure 2B:
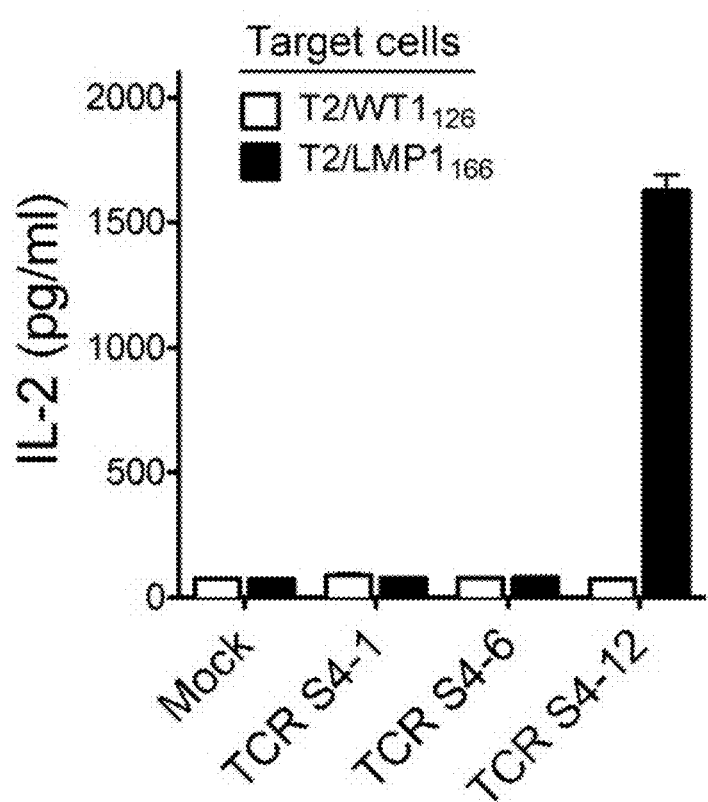

The antigenic specificities of LMP1*166 TCR genes (S4-1, S4-6, S4-12) were determined by assessing the immunological functions of TCR-transferred T cells against the target cells in which MHC molecules are presented with LMP1*166 peptides (i.e., the activation of TCR-transferred T cells after they recognize target antigens) by assessing IL-2 secretion by ELISA. As a result, a group using LMP1*166 S4-12 TCR genes secreted specifically high levels of IL-2 against the target cells treated with LMP1*166 peptides (FIG. 2B).

<Example 3> Verification of Antigenic Specificities of LMP1*166 TCR S4-12-Introduced T Cells In Vitro LMP1*166 S4-12 TCR genes which are highly expressed and exhibit high level of antigenic specificities in human lymphocytes were expressed in human lymphocytes, and in vitro experiments were performed to verify the antigenic specificities and antitumor specificities thereof by measuring IL-2 secretion by ELISA and IFN-γ secretion by ELISPOT. Then, the ability of LMP1*166 S4-12 TCR-expressed human lymphocytes to kill target cells was measured using the cell killing assay with radioactive chromium (51-Cr).

The ELISA to measure IL-2 secretion was performed as follows: $1 \times 10^5$ LMP1*166 TCR-expressed lymphocytes per well, $5 \times 10^4$ T2 or LCL cell lines (sensitized with 5 μg/ml concentration of LMP1*166 peptides and then irradiated at 10,000 rad) and peptides each were combined with K562/HLA-A2/LMP1 cell lines which were unsensitized and irradiated at 10,000 rad using a 96-well cell culture plate, thereby preparing three culture tanks for each combination. After 40 hours of cultivation, a supernatant was obtained. Target cells unsensitized with peptides or sensitized with WT1*126 peptides were used as a control group. The secretion of IL-2 Cytokines in the supernatant was measured using the experimental method used by the manufacturer using ELISA kit (Biolegend).

The ELISPOT assay to measure antigen-specific IFN-γ secretion was performed as follows: $1 \times 10^5$ LMP1*166 TCR-expressed lymphocytes per well, $5 \times 10^4$ T2 or LCL cell lines (sensitized with 5 μg/ml concentration of LMP1*166 peptides and irradiated at 10,000 rad), and peptides were mixed with K562/HLA-A2/LMP1 cell lines which were unsensitized and irradiated at 10,000 rad and cultured using an ELISpotPLUS kit (manufactured by Mabtech). Target cells unsensitized with peptides were used as a control group. 24 hours later, the secretion of IFN-γ in each culture tank was measured.

In addition, to measure the cell-killing ability of LMP1*166 TCR-expressing human lymphocytes, T2 and K562/HLA-A2/LMP1 cell lines sensitized with LMP1*166 peptides having a concentration of 5 μg/ml were used as positive target cells, and T2 cell lines unsensitized with peptides and K562 cell lines expressing only HLA-A*0201 molecules were used as negative target cells. All the target cells were labeled in 0.2 ml RPMI containing 10% FBS for 1 hour at 37° C. at a concentration of 100 μCi 51Cr and then washed four times. Three culture tanks for culturing of 5×10³ target cells per well were prepared using a V-bottom 96-well cell culture plate. Then, LMP1*166 TCR-expressing lymphocytes were mixed at a set E/T (effector-to-target) ratio. The mixture was centrifuged for 2 minutes at 1200 rpm and then cultured in a 96-well cell culture plate at 37° C. Five hours later, a supernatant was collected and γ rays of 51Cr were measured. Percent specific lysis was calculated by the following formula:

% specific lysis=(cpm of experimental release−cpm of spontaneous release)/(cpm of maximal release−cpm of spontaneous release)×100

Figures 3A, 3B:
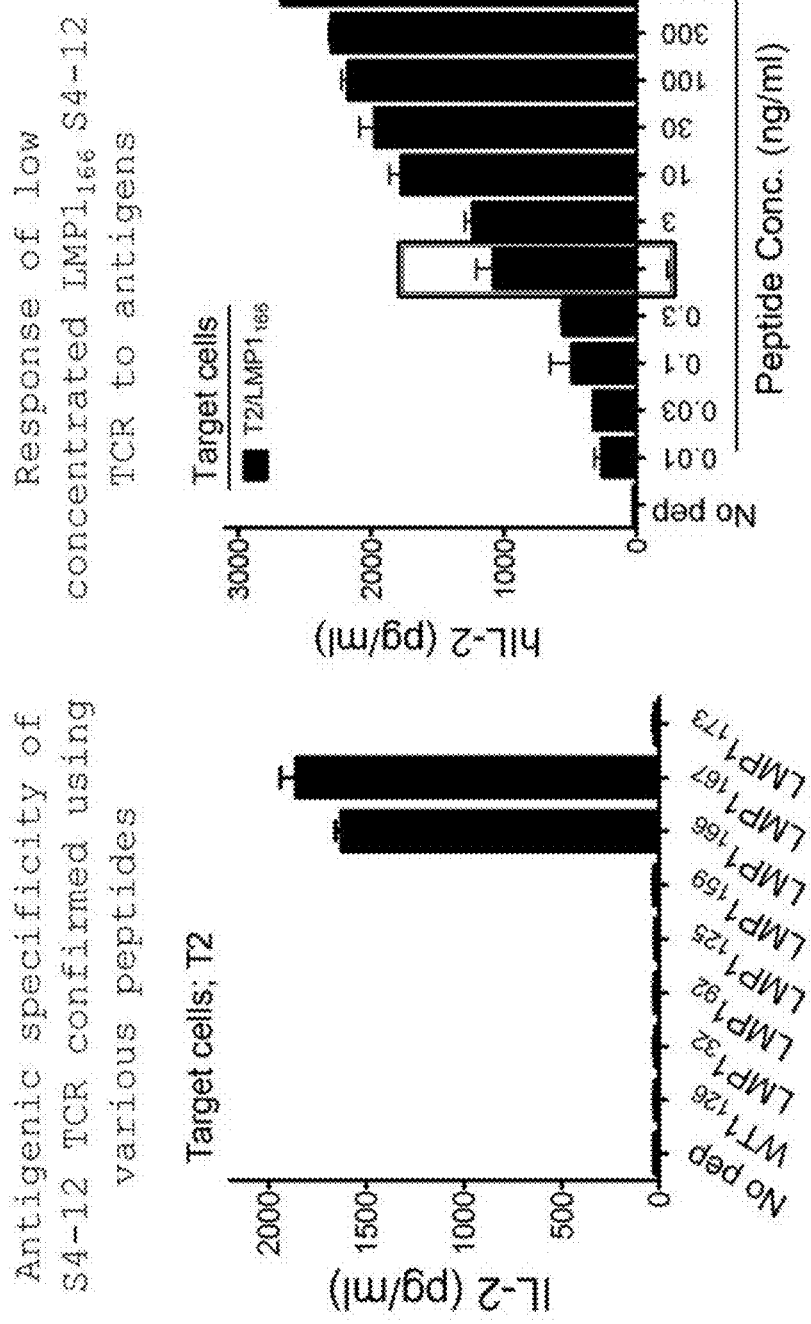
FIGS. 3A-3B shows the antigenic specificity of T cells (FIG. 3A) into which EBV LMP-1-specific TCR (LMP1*166 S4-12) of the present invention is introduced and the reaction of TCR in low concentrations of EBV LMP-1 peptide to antigens (FIG. 3B).

As shown in FIG. 3 regarding the antigenic specificities of LMP1*166 peptides and LMP1*166 S4-12 TCR-introduced T cells according to concentration, LMP1*166 S4-12 TCR-expressing human lymphocytes did not respond to the target cells sensitized with the peptides binding to potential LMP1 antigen-derived HLA-A2 molecules, and responded specifically to the target cells sensitized with LMP1*166(TLLVDLLWL, SEQ ID NO: 1) and LMP1*167(LLVDLLWLL, SEQ ID NO: 25) peptides (each having one amino acid change) (FIG. 3A). LMP1*166 S4-12 TCR-expressing human lymphocytes also responded to the target cells treated with high-affinity LMP1*166 peptides having a concentration as low as 1 ng/ml (FIG. 3B).

Figure 4B:
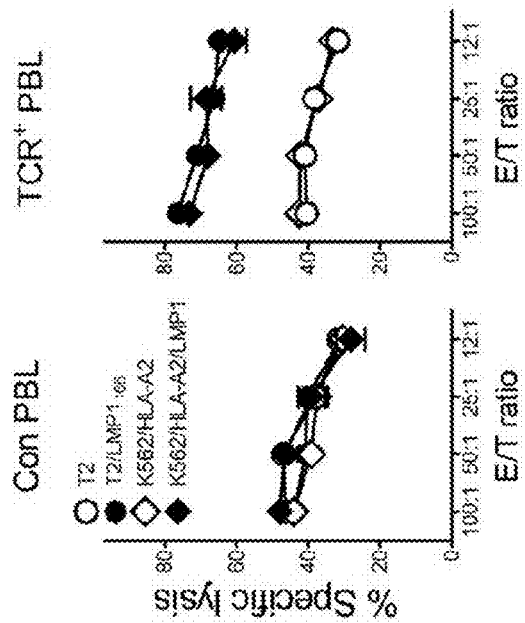
FIGS. 4A-4B shows the antigenic specificity of LMP1*166 S4-12 TCR-introduced T cells, determined by using an IFN-γ-secretion ELISPOT assay (FIG. 4A) and a method for the determination of 51-Cr-cell killing ability (FIG. 4B).
Figure 4A:
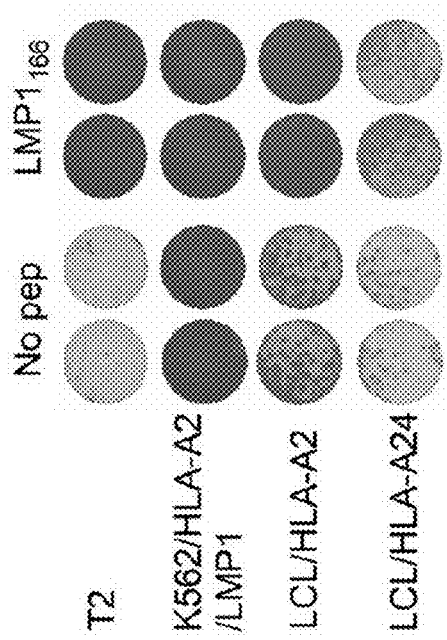

Then, IFN-γ secretion was measured using the ELISPOT assay and the antigenic specificity of LMP1*166 S4-12 TCR-introduced T cells was measured by measuring 51-Cr-cell-killing ability. As a result, it was found that LMP1*166 S4-12 TCR-expressing human lymphocytes responded specifically not only to the target cells expressing HLA-A2 molecules and sensitized with LMP1*166(TLLVDLLWL SEQ ID NO: 1) peptides (T2 and LCL/HLA-A2 cell lines), but also to the target cells (K562/HLA-A2/LMP-1) expressing HLA-A2 molecules that help LMP1*166 peptides present on the surface of the target cells through natural antigen-presenting processes and LMP1 proteins (FIG. 4A). It was also found by measuring $^{51}$Cr cell-killing ability that LMP1*166 S4-12 TCR-expressing human lymphocytes exhibited particularly excellent killing ability against the target cells (K562/HLA-A2/LMP-1) expressing HLA-A2 molecules and LMP1 proteins and the target cell (T2/LMP1*166) expressing HLA-A2 molecules and sensitized with LMP1*166(TLLVDLLWL SEQ ID NO: 1) peptides (FIG. 4B).

Figures 5A, 5B:
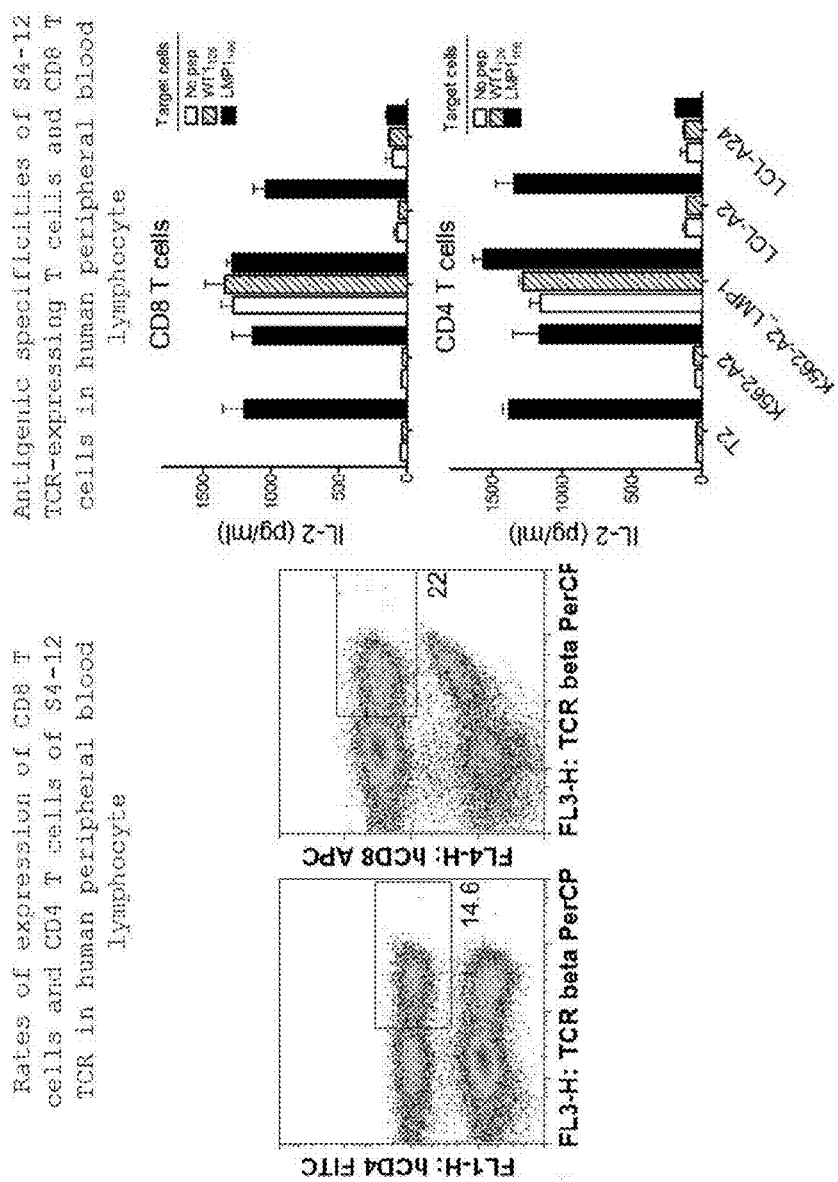
FIGS. 5A-5B shows the rates of expression of CD8 T cells and CD4 T cells into which LMP1*166 S4-12 TCRs are introduced (FIG. 5A) and the antigenic specificity thereof (FIG. 5B).

Lastly, the ratios of the expression of LMP1*166 S4-12 TCR-introduced CD8 T cells and CD4 T cells and the antigenic specificities thereof were measured. As a result, it was found that when LMP1*166 S4-12 TCR genes were transferred to human lymphocytes, they were expressed not only in CD8 T cells but also in CD4 T cells, and that the expression rate was slightly higher in CD8 T cells (FIG. 5A). Such results are commonly observed in most cases of transferring TCR genes to human T cells.

In addition, CD8 T cells and CD4 T cells were isolated from human lymphocytes transferred to LMP1166 S4-12 TCR clones, and the antigenic specificities of the cell groups were measured. As a result, both the CD8 T cell group and CD4 T cell group expressed IL-2 it-2 cytokines, showing high antigenic specificities against the target cells sensitized with LMP1*166(TLLVDLLWL, SEQ ID NO: 1) peptides, and that they responded to K562/A2/LMP1 target cells unsensitized with LMP1*166 peptides or sensitized with other peptides (WT1*126) by helping LMP1*166 peptides present on the surface of the target cells through natural antigen-presenting processes (FIG. 5B).

<Example 4> Verification of the Efficacy of LMP1*166 TCR S4-12-Introduced T Cells for the Treatment of Tumors Using Immunodeficient Mice The efficacy of LMP1*166 TCR S4-12-introduced T cells for the treatment of tumors was verified using immunodeficient mice (NSG mouse; NOD.Cg-Prkdcscid Il2rgtm1Wjl/SzJ) which can substitute for human tumor models. The experimental mice were purchased from Jackson Laboratory for use in experiments approved by the Animal Experiment Committee of the Catholic University.

5×10⁶ K562/HLA-A2/LMP-1 cell lines (tumor cell lines expressing HLA-A2 molecules and LMP1 proteins) were injected intravenously into the immunodeficient mice which were irradiated at 300 rad 20 hours earlier (four mice per group). Seven days later, 2×10⁷ LMP1*166 TCR S4-12-expressing human lymphocytes were injected intravenously (adaptive injection), and then the survival rate of the immunodeficient mice was examined. A group of mice which were not adoptively injected with human lymphocytes and another group of mice which were adoptively injected with human lymphocytes to which LMP1*166 TCRs were not transferred were used as control groups. The existence of human T cells in peripheral blood of the mice of all groups was examined by FACS using human CD45 antibodies and mouse CD45 antibodies.

Figure 6B:
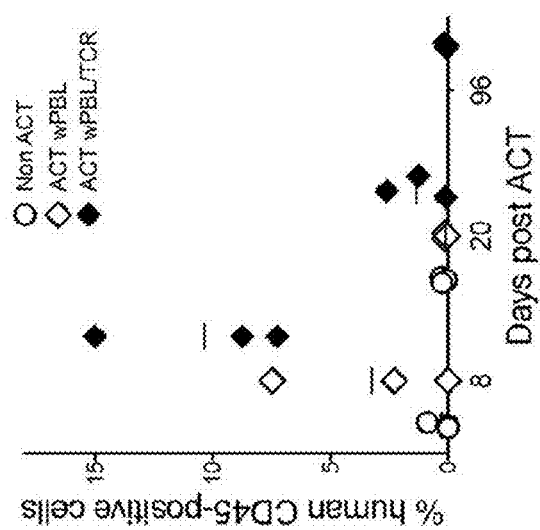
FIGS. 6A-6B shows the survival of immunodeficient mice injected adoptively with LMP1*166 TCR S4-12-introduced T cells (FIG. 6A) and the rate of retention of the T cells in mouse peripheral blood (FIG. 6B).
Figure 6A:
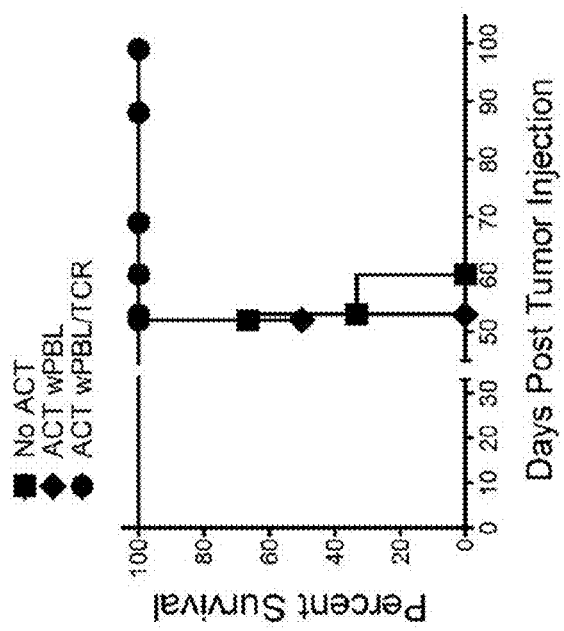

As shown in FIG. 6A, the mice of the group (No ACT) which were not adoptively injected with T cells and the mice of the group (ACT wPBL) which were adoptively injected with T cells to which LMP1*166 TCRs S4-12 genes were not transferred were all dead within 60 days after the tumor injection. However, the mice of the group (ACT wPBL/TCR) which were adoptively injected with T cells to which LMP1*166 TCR S4-12 genes were introduced survived beyond 90 days after the tumor injection.

Further, peripheral blood was collected from immunodeficient mice, and then the existence of human T cells was examined therein by FACS. As a result, the mice of the group (ACT wPBL/TCR) which were adoptively injected with T cells to which LMP1*166 TCR S4-12 genes were introduced had a higher rate of human T cells, which existed for more than 95 days, compared to the mice of the group (ACT wPBL) which were adoptively injected with T cells to which LMP1*166 TCR S4-12 genes were not introduced (FIG. 6B). The results indicate that T cells to which LMP1*166 TCR S4-12 genes were introduced act as an important immunocyte having antitumor activity.

What is claimed is:

1. A method for treating EBV-associated diseases in a subject in need thereof, comprising
administering a pharmaceutically effective amount of the vector comprising a nucleotide sequence encoding the T-cell receptor to the subject in need thereof,
wherein the T-cell receptor comprises a α-chain and a β-chain, wherein the α-chain comprises complementarity determining regions (CDRs) of SEQ ID NO: 3 (CDR1α), SEQ ID NO: 4 (CDR2α), and SEQ ID NO: 5 (CDR3α), and wherein the β-chain comprises CDRs of SEQ ID NO: 7 (CDR1β), SEQ ID NO: 8 (CDR2β), and SEQ ID NO: 9 (CDR3β),
and
wherein the T-cell receptor specifically binds to a latent membrane protein 1 (LMP1) epitope of an Epstein-Barr Virus (EBV) of SEQ ID NO: 1.

2. The method of claim 1, wherein the T-cell receptor of claim 1, wherein the α-chain of the T-cell receptor comprises the amino acid sequence of SEQ ID NO: 2.

3. The method of claim 1, wherein the T-cell receptor of claim 1, wherein the β-chain of the T-cell receptor comprises the amino acid sequence of SEQ ID NO: 6.

4. The method of claim 1, wherein the nucleotide sequence comprises a nucleotide sequence of a base sequence of SEQ ID NO: 10 encoding an α-chain of the T cell receptor, and a base sequence of a nucleotide sequence of SEQ ID NO: 14 encoding an β-chain of the T-cell receptor.

5. The method of claim 1, wherein the EBV-associated disease is EBV-positive Hodgkin lymphoma, EBV-positive nasopharyngeal carcinoma, or EBV-positive post-transplant lymphoproliferative disease (PTLD).

* * * * *

SEQUENCE LISTING

<160> NUMBER OF SEQ ID NOS: 31

<210> SEQ ID NO 1
<211> LENGTH: 9

```
<212> TYPE: PRT
<213> ORGANISM: Artificial Sequence
<220> FEATURE:
<223> OTHER INFORMATION: LMP-1 a.a. 166-174  from Epstein-Barr Virus
      (LMP1*166)

<400> SEQUENCE: 1

Thr Leu Leu Val Asp Leu Leu Trp Leu
1               5

<210> SEQ ID NO 2
<211> LENGTH: 270
<212> TYPE: PRT
<213> ORGANISM: Artificial Sequence
<220> FEATURE:
<223> OTHER INFORMATION: Alpha chain of LMP1*166 S4-12 mTCR

<400> SEQUENCE: 2

Met Lys Thr Val Thr Gly Pro Leu Phe Leu Cys Phe Trp Leu Gln Leu
1               5                   10                  15

Asn Cys Val Ser Arg Gly Glu Gln Val Glu Gln Arg Pro Pro His Leu
            20                  25                  30

Ser Val Arg Glu Gly Asp Ser Ala Val Ile Ile Cys Thr Tyr Thr Asp
        35                  40                  45

Pro Asn Ser Tyr Tyr Phe Phe Trp Tyr Lys Gln Glu Pro Gly Ala Gly
    50                  55                  60

Leu Gln Leu Leu Met Lys Val Phe Ser Ser Thr Glu Ile Asn Glu Gly
65                  70                  75                  80

Gln Gly Phe Thr Val Leu Leu Asn Lys Lys Asp Lys Gln Leu Ser Leu
                85                  90                  95

Asn Leu Thr Ala Ala His Pro Gly Asp Ser Ala Val Tyr Phe Cys Ala
            100                 105                 110

Val Ser Gly Thr Gly Gly Tyr Lys Val Val Phe Gly Ser Gly Thr Arg
        115                 120                 125

Leu Leu Val Ser Pro Asp Ile Gln Asn Pro Glu Pro Ala Val Tyr Gln
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Thr Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Ser Val Met Gly Leu Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 3
<211> LENGTH: 6
<212> TYPE: PRT
<213> ORGANISM: Artificial Sequence
<220> FEATURE:
<223> OTHER INFORMATION: CDR 1 of alpha chain of LMP1*166 S4-12 mTCR
```

<400> SEQUENCE: 3

Asp Pro Asn Ser Tyr Tyr
1               5

<210> SEQ ID NO 4
<211> LENGTH: 7
<212> TYPE: PRT
<213> ORGANISM: Artificial Sequence
<220> FEATURE:
<223> OTHER INFORMATION: CDR 2 of alpha chain of LMP1*166 S4-12 mTCR

<400> SEQUENCE: 4

Val Phe Ser Ser Thr Glu Ile
1               5

<210> SEQ ID NO 5
<211> LENGTH: 11
<212> TYPE: PRT
<213> ORGANISM: Artificial Sequence
<220> FEATURE:
<223> OTHER INFORMATION: CDR 3 of alpha chain of LMP1*166 S4-12 mTCR

<400> SEQUENCE: 5

Ala Val Ser Gly Thr Gly Gly Tyr Lys Val Val
1               5                   10

<210> SEQ ID NO 6
<211> LENGTH: 306
<212> TYPE: PRT
<213> ORGANISM: Artificial Sequence
<220> FEATURE:
<223> OTHER INFORMATION: Beta chain of LMP1*166 S4-12 mTCR

<400> SEQUENCE: 6

Met Ala Thr Arg Leu Leu Cys Tyr Thr Val Leu Cys Leu Leu Gly Ala
1               5                   10                  15

Arg Ile Leu Asn Ser Lys Val Ile Gln Thr Pro Arg Tyr Leu Val Lys
                20                  25                  30

Gly Gln Gly Gln Lys Ala Lys Met Arg Cys Ile Pro Glu Lys Gly His
            35                  40                  45

Pro Val Val Phe Trp Tyr Gln Gln Asn Lys Asn Asn Glu Phe Lys Phe
        50                  55                  60

Leu Ile Asn Phe Gln Asn Gln Glu Val Leu Gln Gln Ile Asp Met Thr
65                  70                  75                  80

Glu Lys Arg Phe Ser Ala Glu Cys Pro Ser Asn Ser Pro Cys Ser Leu
                85                  90                  95

Glu Ile Gln Ser Ser Glu Ala Gly Asp Ser Ala Leu Tyr Leu Cys Ala
            100                 105                 110

Ser Asn Gln Leu Gly Ser Ser Tyr Glu Gln Tyr Phe Gly Pro Gly Thr
        115                 120                 125

Arg Leu Thr Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg

-continued

```
               195                 200                 205
Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
    290                 295                 300

Asn Ser
305

<210> SEQ ID NO 7
<211> LENGTH: 5
<212> TYPE: PRT
<213> ORGANISM: Artificial Sequence
<220> FEATURE:
<223> OTHER INFORMATION: CDR 1 of beta chain of LMP1*166 S4-12 mTCR

<400> SEQUENCE: 7

Lys Gly His Pro Val
1               5

<210> SEQ ID NO 8
<211> LENGTH: 6
<212> TYPE: PRT
<213> ORGANISM: Artificial Sequence
<220> FEATURE:
<223> OTHER INFORMATION: CDR 2 of beta chain of LMP1*166 S4-12 mTCR

<400> SEQUENCE: 8

Phe Gln Asn Gln Glu Val
1               5

<210> SEQ ID NO 9
<211> LENGTH: 12
<212> TYPE: PRT
<213> ORGANISM: Artificial Sequence
<220> FEATURE:
<223> OTHER INFORMATION: CDR 3 of beta chain of LMP1*166 S4-12 mTCR

<400> SEQUENCE: 9

Ala Ser Asn Gln Leu Gly Ser Ser Tyr Glu Gln Tyr
1               5                   10

<210> SEQ ID NO 10
<211> LENGTH: 810
<212> TYPE: DNA
<213> ORGANISM: Artificial Sequence
<220> FEATURE:
<223> OTHER INFORMATION: Alpha chain of LMP1*166 S4-12 mTCR

<400> SEQUENCE: 10
atgaagacag tgactggacc tttgttcctg tgcttctggc tgcagctgaa ctgtgtgagc     60
agaggcgagc aggtggagca gcgcccctcc tcacctgagtg tccgggaggg agacagtgcc    120
gttatcatct gcacctacac agaccctaac agttattact tcttctggta caagcaagag    180
ccgggggcag tcttcagtt gcttatgaag gttttctcaa gtacggaaat aaacgaagga    240
```

```
caaggattca ctgtcctact gaacaagaaa gacaaacaac tctctctgaa cctcacagct    300
gcccatcctg gggactcagc cgtgtacttc tgcgcagtct ccgggactgg aggctataaa    360
gtggtctttg gaagtgggac tcgattgctg gtaagccctg acatccagaa cccagaacct    420
gctgtgtacc agttaaaaga tcctcggtct caggacagca ccctctgcct gttcaccgac    480
tttgactccc aaatcaatgt gccgaaaacc atggaatctg gaacgttcat cactgacaaa    540
actgtgctgg acatgaaagc tatggattcc aagagcaatg ggccattgc ctggagcaac     600 cagacaagct tcacctgcca agatatcttc aaagagacca cgccaccta ccccagttca     660 gacgttccct gtgatgccac gttgactgag aaaagctttg aaacagatat gaacctaaac    720
tttcaaaacc tgtcagttat gggactccga atcctcctgc tgaaagtagc cggatttaac    780
ctgctcatga cgctgaggct gtggtccagt                                      810

<210> SEQ ID NO 11
<211> LENGTH: 18
<212> TYPE: DNA
<213> ORGANISM: Artificial Sequence
<220> FEATURE:
<223> OTHER INFORMATION: CDR 1 of alpha chain of LMP1*166 S4-12 mTCR

<400> SEQUENCE: 11
gaccctaaca gttattac                                                   18

<210> SEQ ID NO 12
<211> LENGTH: 21
<212> TYPE: DNA
<213> ORGANISM: Artificial Sequence
<220> FEATURE:
<223> OTHER INFORMATION: CDR 2 of alpha chain of LMP1*166 S4-12 mTCR

<400> SEQUENCE: 12
gttttctcaa gtacggaaat a                                               21

<210> SEQ ID NO 13
<211> LENGTH: 33
<212> TYPE: DNA
<213> ORGANISM: Artificial Sequence
<220> FEATURE:
<223> OTHER INFORMATION: CDR 3 of alpha chain of LMP1*166 S4-12 mTCR

<400> SEQUENCE: 13
gcagtctccg ggactggagg ctataaagtg gtc                                  33

<210> SEQ ID NO 14
<211> LENGTH: 921
<212> TYPE: DNA
<213> ORGANISM: Artificial Sequence
<220> FEATURE:
<223> OTHER INFORMATION: Beta chain of LMP1*166 S4-12 mTCR

<400> SEQUENCE: 14
atggctacaa ggctcctctg ttacacagta ctttgtctcc tgggtgcaag aattttgaat    60
tcaaaagtca ttcagactcc aagatatctg gtgaaagggc aaggacaaaa agcaaagatg    120
aggtgtatcc ctgaaaaggg acatccagtt gtattctggt atcaacaaaa taagaacaat    180
gagtttaaat ttttgattaa ctttcagaat caagaagttc ttcagcaaat agacatgact    240
gaaaaacgat tctctgctga gtgtccttca aactcacctt gcagcctaga aattcagtcc    300
tctgaggcag gagactcagc actgtacctc tgtgccagca accaactggg gtcctcctat    360
```

```
gaacagtact tcggtcccgg caccaggctc acggttttag aggatctgag aaatgtgact    420
ccacccaagg tctccttgtt tgagccatca aaagcagaga ttgcaaacaa acaaaaggct    480
accctcgtgt gcttggccag gggcttcttc cctgaccacg tggagctgag ctggtgggtg    540
aatggcaagg aggtccacag tggggtcagc acggaccctc aggcctacaa ggagagcaat    600
tatagctact gcctgagcag ccgcctgagg gtctctgcta ccttctggca caatcctcga    660
aaccacttcc gctgccaagt gcagttccat gggctttcag aggaggacaa gtggccagag    720
ggctcaccca aacctgtcac acagaacatc agtgcagagg cctggggccg agcagactgt    780
ggaatcactt cagcatccta tcatcagggg gttctgtctg caaccatcct ctatgagatc    840
ctactgggga aggccaccct atatgctgtg ctggtcagtg cctggtgct gatggccatg    900 gtcaagaaaa aaaattcctg a                                              921
```

```
<210> SEQ ID NO 15
<211> LENGTH: 15
<212> TYPE: DNA
<213> ORGANISM: Artificial Sequence
<220> FEATURE:
<223> OTHER INFORMATION: CDR 1 of beta chain of LMP1*166 S4-12 mTCR

<400> SEQUENCE: 15
aagggacatc cagtt                                                      15

<210> SEQ ID NO 16
<211> LENGTH: 18
<212> TYPE: DNA
<213> ORGANISM: Artificial Sequence
<220> FEATURE:
<223> OTHER INFORMATION: CDR 2 of beta chain of LMP1*166 S4-12 mTCR

<400> SEQUENCE: 16
tttcagaatc aagaagtt                                                   18

<210> SEQ ID NO 17
<211> LENGTH: 36
<212> TYPE: DNA
<213> ORGANISM: Artificial Sequence
<220> FEATURE:
<223> OTHER INFORMATION: CDR 3 of beta chain of LMP1*166 S4-12 mTCR

<400> SEQUENCE: 17
gccagcaacc aactgggggtc ctcctatgaa cagtac                              36

<210> SEQ ID NO 18
<211> LENGTH: 602
<212> TYPE: PRT
<213> ORGANISM: Artificial Sequence
<220> FEATURE:
<223> OTHER INFORMATION: LMP1*166 S4-12   TCRAlpha P2A TCRBeta

<400> SEQUENCE: 18
```

Met Lys Thr Val Thr Gly Pro Leu Phe Leu Cys Phe Trp Leu Gln Leu
1               5                   10                  15

Asn Cys Val Ser Arg Gly Glu Gln Val Glu Gln Arg Pro Pro His Leu
            20                  25                  30

Ser Val Arg Glu Gly Asp Ser Ala Val Ile Ile Cys Thr Tyr Thr Asp
        35                  40                  45

Pro Asn Ser Tyr Tyr Phe Phe Trp Tyr Lys Gln Glu Pro Gly Ala Gly
    50                  55                  60

Leu Gln Leu Leu Met Lys Val Phe Ser Ser Thr Glu Ile Asn Glu Gly

```
             65                  70                  75                  80
Gln Gly Phe Thr Val Leu Leu Asn Lys Lys Asp Lys Gln Leu Ser Leu
                    85                  90                  95

Asn Leu Thr Ala Ala His Pro Gly Asp Ser Ala Val Tyr Phe Cys Ala
                   100                 105                 110

Val Ser Gly Thr Gly Gly Tyr Lys Val Val Phe Gly Ser Gly Thr Arg
                   115                 120                 125

Leu Leu Val Ser Pro Asp Ile Gln Asn Pro Glu Pro Ala Val Tyr Gln
            130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                    165                 170                 175

Ile Thr Asp Lys Thr Val Leu Asp Met Lys Ala Met Asp Ser Lys Ser
                180                 185                 190

Asn Gly Ala Ile Ala Trp Ser Asn Gln Thr Ser Phe Thr Cys Gln Asp
            195                 200                 205

Ile Phe Lys Glu Thr Asn Ala Thr Tyr Pro Ser Ser Asp Val Pro Cys
        210                 215                 220

Asp Ala Thr Leu Thr Glu Lys Ser Phe Glu Thr Asp Met Asn Leu Asn
225                 230                 235                 240

Phe Gln Asn Leu Ser Val Met Gly Leu Arg Ile Leu Leu Leu Lys Val
                245                 250                 255

Ala Gly Phe Asn Leu Leu Met Thr Leu Arg Leu Trp Ser Ser Arg Val
                260                 265                 270

Lys Arg Gly Ser Gly Ala Thr Asn Phe Ser Leu Leu Lys Gln Ala Gly
            275                 280                 285

Asp Val Glu Glu Asn Pro Gly Pro Met Ala Thr Arg Leu Leu Cys Tyr
        290                 295                 300

Thr Val Leu Cys Leu Leu Gly Ala Arg Ile Leu Asn Ser Lys Val Ile
305                 310                 315                 320

Gln Thr Pro Arg Tyr Leu Val Lys Gly Gln Gly Gln Lys Ala Lys Met
                325                 330                 335

Arg Cys Ile Pro Glu Lys Gly His Pro Val Val Phe Trp Tyr Gln Gln
                340                 345                 350

Asn Lys Asn Asn Glu Phe Lys Phe Leu Ile Asn Phe Gln Asn Gln Glu
            355                 360                 365

Val Leu Gln Gln Ile Asp Met Thr Glu Lys Arg Phe Ser Ala Glu Cys
        370                 375                 380

Pro Ser Asn Ser Pro Cys Ser Leu Glu Ile Gln Ser Ser Glu Ala Gly
385                 390                 395                 400

Asp Ser Ala Leu Tyr Leu Cys Ala Ser Asn Leu Gly Ser Ser Tyr
                405                 410                 415

Glu Gln Tyr Phe Gly Pro Gly Thr Arg Leu Thr Val Leu Glu Asp Leu
                420                 425                 430

Arg Asn Val Thr Pro Pro Lys Val Ser Leu Phe Glu Pro Ser Lys Ala
            435                 440                 445

Glu Ile Ala Asn Lys Gln Lys Ala Thr Leu Val Cys Leu Ala Arg Gly
        450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Ala Tyr Lys Glu Ser Asn
                485                 490                 495
```

Tyr Ser Tyr Cys Leu Ser Ser Arg Leu Arg Val Ser Ala Thr Phe Trp
            500                 505                 510

His Asn Pro Arg Asn His Phe Arg Cys Gln Val Gln Phe His Gly Leu
            515                 520                 525

Ser Glu Glu Asp Lys Trp Pro Glu Gly Ser Pro Lys Pro Val Thr Gln
            530                 535                 540

Asn Ile Ser Ala Glu Ala Trp Gly Arg Ala Asp Cys Gly Ile Thr Ser
545                 550                 555                 560

Ala Ser Tyr His Gln Gly Val Leu Ser Ala Thr Ile Leu Tyr Glu Ile
                565                 570                 575

Leu Leu Gly Lys Ala Thr Leu Tyr Ala Val Leu Val Ser Gly Leu Val
            580                 585                 590

Leu Met Ala Met Val Lys Lys Lys Asn Ser
            595                 600

<210> SEQ ID NO 19
<211> LENGTH: 1812
<212> TYPE: DNA
<213> ORGANISM: Artificial Sequence
<220> FEATURE:
<223> OTHER INFORMATION: LMP1*166 S4-12  TCRAlpha P2A TCRBeta

<400> SEQUENCE: 19
atgaagacag tgactggacc tttgttcctg tgcttctggc tgcagctgaa ctgtgtgagc      60
agaggcgagc aggtggagca gcgccctcct cacctgagtg tccgggaggg agacagtgcc     120
gttatcatct gcacctacac agaccctaac agttattact tcttctggta caagcaagag     180 ccggggggcag gtcttcagtt gcttatgaag gttttctcaa gtacggaaat aaacgaagga     240
caaggattca ctgtcctact gaacaagaaa gacaaacaac tctctctgaa cctcacagct     300
gcccatcctg ggactcagc cgtgtacttc tgcgcagtct ccgggactgg aggctataaa     360
gtggtctttg gaagtgggac tcgattgctg gtaagccctg acatccagaa cccagaacct     420
gctgtgtacc agttaaaaga tcctcggtct caggacagca ccctctgcct gttcaccgac     480
tttgactccc aaatcaatgt gccgaaaacc atggaatctg gaacgttcat cactgacaaa     540
actgtgctgg acatgaaagc tatggattcc aagagcaatg gggccattgc ctggagcaac     600
cagacaagct tcacctgcca agatatcttc aaagagacca acgccaccta ccccagttca     660
gacgttccct gtgatgccac gttgactgag aaaagctttg aaacagatat gaacctaaac     720
tttcaaaacc tgtcagttat gggactccga atcctcctgc tgaaagtagc cggatttaac     780
ctgctcatga cgctgaggct gtggtccagt agagtgaaga gaggcagcgg cgccaccaac     840
ttctccctgc tgaagcaggc cggcgacgtg aagaaaacc ctggccccat ggctacaagg     900
ctcctctgtt acacagtact tgtctcctg ggtgcaagaa ttttgaattc aaaagtcatt     960
cagactccaa gatatctggt gaaagggcaa ggacaaaaag caagatgag gtgtatccct     1020 gaaaagggac atccagttgt attctggtat caacaaaata gaacaatga gtttaaattt     1080 ttgattaact tcagaatca agaagttctt cagcaaatag acatgactga aaaacgattc     1140
tctgctgagt gtccttcaaa ctcaccttgc agcctagaaa ttcagtcctc tgaggcagga     1200
gactcagcac tgtacctctg tgccagcaac caactggggt cctccatga acagtacttc     1260 ggtcccggca ccaggctcac ggttttagag atctgagaa atgtgactcc acccaaggtc     1320
tccttgtttg agccatcaaa agcagagatt gcaaacaaac aaaaggctac cctcgtgtgc     1380
ttggccaggg gcttcttccc tgaccacgtg agctgagct ggtgggtgaa tggcaaggag     1440

```
gtccacagtg gggtcagcac ggaccctcag gcctacaagg agagcaatta tagctactgc    1500
ctgagcagcc gcctgagggt ctctgctacc ttctggcaca atcctcgaaa ccacttccgc    1560
tgccaagtgc agttccatgg gctttcagag gaggacaagt ggccagaggg ctcacccaaa    1620
cctgtcacac agaacatcag tgcagaggcc tggggccgag cagactgtgg aatcacttca    1680
gcatcctatc atcaggggt tctgtctgca accatcctct atgagatcct actggggaag     1740
gccaccctat atgctgtgct ggtcagtggc ctggtgctga tggccatggt caagaaaaaa    1800
aattcctgat aa                                                        1812
```

```
<210> SEQ ID NO 20
<211> LENGTH: 9
<212> TYPE: PRT
<213> ORGANISM: Artificial Sequence
<220> FEATURE:
<223> OTHER INFORMATION: WT1*126

<400> SEQUENCE: 20

Arg Met Phe Pro Asn Ala Pro Tyr Leu
1               5

<210> SEQ ID NO 21
<211> LENGTH: 9
<212> TYPE: PRT
<213> ORGANISM: Artificial Sequence
<220> FEATURE:
<223> OTHER INFORMATION: LMP1*32

<400> SEQUENCE: 21

Leu Leu Leu Ala Leu Leu Phe Trp Leu
1               5

<210> SEQ ID NO 22
<211> LENGTH: 9
<212> TYPE: PRT
<213> ORGANISM: Artificial Sequence
<220> FEATURE:
<223> OTHER INFORMATION: LMP1*92

<400> SEQUENCE: 22

Leu Leu Leu Ile Ala Leu Trp Asn Leu
1               5

<210> SEQ ID NO 23
<211> LENGTH: 9
<212> TYPE: PRT
<213> ORGANISM: Artificial Sequence
<220> FEATURE:
<223> OTHER INFORMATION: LMP1*125

<400> SEQUENCE: 23

Tyr Leu Leu Glu Met Leu Trp Arg Leu
1               5

<210> SEQ ID NO 24
<211> LENGTH: 9
<212> TYPE: PRT
<213> ORGANISM: Artificial Sequence
<220> FEATURE:
<223> OTHER INFORMATION: LMP1*125

<400> SEQUENCE: 24

Tyr Leu Gln Gln Asn Trp Trp Thr Leu
1               5
```

<210> SEQ ID NO 25
<211> LENGTH: 9
<212> TYPE: PRT
<213> ORGANISM: Artificial Sequence
<220> FEATURE:
<223> OTHER INFORMATION: LMP1*167

<400> SEQUENCE: 25

Leu Leu Val Asp Leu Leu Trp Leu Leu
1               5

<210> SEQ ID NO 26
<211> LENGTH: 9
<212> TYPE: PRT
<213> ORGANISM: Artificial Sequence
<220> FEATURE:
<223> OTHER INFORMATION: LMP1*173

<400> SEQUENCE: 26

Trp Leu Leu Leu Phe Leu Ala Ile Leu
1               5

<210> SEQ ID NO 27
<211> LENGTH: 22
<212> TYPE: DNA
<213> ORGANISM: Artificial Sequence
<220> FEATURE:
<223> OTHER INFORMATION: TCR-alpha constant region primer

<400> SEQUENCE: 27
actggtacac agcaggttct gg                                              22

<210> SEQ ID NO 28
<211> LENGTH: 21
<212> TYPE: DNA
<213> ORGANISM: Artificial Sequence
<220> FEATURE:
<223> OTHER INFORMATION: TCR-beta constant region primer

<400> SEQUENCE: 28
aaggagacct tgggtggagt c                                               21

<210> SEQ ID NO 29
<211> LENGTH: 26
<212> TYPE: PRT
<213> ORGANISM: Artificial Sequence
<220> FEATURE:
<223> OTHER INFORMATION: 2A amino acid sequence

<400> SEQUENCE: 29

Arg Val Lys Arg Gly Ser Gly Ala Thr Asn Phe Ser Leu Leu Lys Gln
1               5                   10                  15

Ala Gly Asp Val Glu Glu Asn Pro Gly Pro
            20                  25

<210> SEQ ID NO 30
<211> LENGTH: 85
<212> TYPE: DNA
<213> ORGANISM: Artificial Sequence
<220> FEATURE:
<223> OTHER INFORMATION: TCR-alpha reverse primer

<400> SEQUENCE: 30
cttccacgtc gccggcctgc ttcagcaggg agaagttggt ggcgccgctg cctctcttca    60

```
ctctactgga ccacagcctc agcgt                                                     85

<210> SEQ ID NO 31
<211> LENGTH: 48
<212> TYPE: DNA
<213> ORGANISM: Artificial Sequence
<220> FEATURE:
<223> OTHER INFORMATION: TCR-beta reverse primer

<400> SEQUENCE: 31
ttctccctgc tgaagcaggc cggcgacgtg gaagaaaacc ctggcccc                            48
```